United States Patent
Ruggiero (10) Patent No.: US 11,969,452 B2
(45) Date of Patent: Apr. 30, 2024

(54) PROCESSES, METHODS AND RATIONALE FOR MANUFACTURING PRE-PROBIOTIC DIETARY SUPPLEMENTS AIMED AT PROTECTING THE HUMAN BODY FROM THE HARMFUL EFFECTS OF ELECTROMAGNETIC RADIATIONS THROUGH QUANTUM ENTANGLEMENT OF DNA REPAIR GENES ELICITED BY NATURAL SUPERLUMINAL PARTICLES INDUCING PHOTOSYNTHESIS VIA CHERENKOV EFFECT

(71) Applicant: Marco Ruggiero, Gilbert, AZ (US)

(72) Inventor: Marco Ruggiero, Gilbert, AZ (US)

(73) Assignee: Marco Ruggiero, Gilbert, AZ (US)

( * ) Notice: Subject to any disclaimer, the term of this patent is extended or adjusted under 35 U.S.C. 154(b) by 89 days.

(21) Appl. No.: 17/343,501

(22) Filed: Jun. 9, 2021

(65) Prior Publication Data
US 2022/0401502 A1    Dec. 22, 2022

(51) Int. Cl.
| | | |
|---|---|---|
| *A61P 39/00* | (2006.01) | |
| *A61K 9/00* | (2006.01) | |
| *A61K 9/06* | (2006.01) | |
| *A61K 9/19* | (2006.01) | |
| *A61K 35/748* | (2015.01) | |
| *A61K 36/11* | (2006.01) | |

(52) U.S. Cl.
CPC ............ *A61K 36/11* (2013.01); *A61K 9/0014* (2013.01); *A61K 9/06* (2013.01); *A61K 35/748* (2013.01); *A61P 39/00* (2018.01)

(58) Field of Classification Search
CPC ........ A61K 36/11; A61K 9/0014; A61K 9/06; A61K 35/748; A61K 9/4858; A61K 9/19; A61K 47/02; A61K 47/26; A61K 47/46; A61P 39/00

See application file for complete search history.

(56) References Cited

PUBLICATIONS

Dwi, Susilaningsih, et al. "Utilization of cyanobacterial biomass from water bloom for bioproduction of lactic acid." World Journal of Microbiology and Biotechnology 17.3 (2001): 259-264. (Year: 2001).*
Ruggiero M., "Experimental evidence for the role of natural radioactivity in influencing viability of commensal microorganisms", bioRxiv preprint (doi: https://doi.org/10.1101/2020.07.21.214676); this version posted on Jul. 22, 2020, total pp. 1-32. (Year: 2020).*
Ruggiero M. Experimental evidence for the role of natural radioactivity in influencing viability of commensal microorganisms. bioRxiv preprint. doi: https://doi.org/10.1101/2020.07.21.214676. Posted on Jul. 22, 2020. Total pp. 1-32. Year 2020.
Ruggiero M. (2021). Experimental Evidence for the Role of Natural Radioactivity in Influencing Viability of Commensal Microorganisms. American Journal of Immunology, 17(1), 14-24. DOI:https://doi.org/10.3844/ajisp.2021.14.24.

\* cited by examiner

*Primary Examiner* — Satyendra K Singh (57) ABSTRACT

This invention is a process to manufacture a probiotic food supplement that can protect the human body from the harmful effects of ionizing and non-ionizing electromagnetic radiations such as gamma and X rays, as well as radio waves.

1 Claim, 1 Drawing Sheet

PROCESSES, METHODS AND RATIONALE FOR MANUFACTURING PRE-PROBIOTIC DIETARY SUPPLEMENTS AIMED AT PROTECTING THE HUMAN BODY FROM THE HARMFUL EFFECTS OF ELECTROMAGNETIC RADIATIONS THROUGH QUANTUM ENTANGLEMENT OF DNA REPAIR GENES ELICITED BY NATURAL SUPERLUMINAL PARTICLES INDUCING PHOTOSYNTHESIS VIA CHERENKOV EFFECT

CROSS-REFERENCE TO RELATED U.S. APPLICATIONS DATA

This application claims the benefit of U.S. Provisional Patent Application No. 63/037,549. EFS ID. 39686529. Confirmation No. 6309. Filed on Jun. 10, 2020.

GOVERNMENT CONTRACT

Not applicable

STATEMENT RE. FEDERALLY SPONSORED RESEARCH/DEVELOPMENT

Not applicable

COPYRIGHT & TRADEMARK NOTICES

A portion of the disclosure of this patent document may contain material which is subject to copyright protection. This patent document may show and/or describe matter which is or mat become trade dress of the owner. The copyright and trade dress owner has no objection to the facsimile reproduction by any one of the patent document or the patent disclosure, as it appears in the Patent and Trademark Office patent files or records, but otherwise reserves all copyrights and trade dress rights whatsoever.

TECHNICAL FIELD

This invention relates to the processes, methods and rationale to manufacture pre-probiotic products that have the goal of protecting the human body from the harmful effects of electromagnetic radiations. These include ionizing radiations such as gamma- or X-rays as well as non-ionizing radiations such as radio waves such as those used for mobile telecommunication comprising the fifth generation technology standard for cellular networks, also known as 5G.

PRIOR ART

Ruggiero M (July 2020: cited as reference 1 on Information Disclosure Statement, form PTO/SB/08b) Experimental evidence for the role of natural radioactivity in influencing viability of commensal microorganisms. bioRxiv preprint. doi: https://doi.org/10.1101/2020.07.21.214676. Posted on Jul. 22, 2020. Total pages 1-32. Year 2020. This version posted on Jul. 22, 2020, discloses the concept of using natural radioactivity in increasing viability and growth of probiotic microorganims, and co-culturing with prebiotic microorganisms *Arthrospira* in carbonated mineral water in order to obtain resistance to the harmful effects of radiations to human cells using *Lactococcus* phage-encoded protein, ORF252; see Abstract, and entire section "Discussion" in Particular). Please notice: this article was posted on the pre-print server bioRxiv after the filing of the provisional application concerning this invention, as specified in paragraph 0001 that reads "This application claims the benefit of U.S. Provisional Patent Application No. 63/037,549. EFS ID. 39686529. Confirmation No. 6309. Filed on Jun. 10, 2020."

Ruggiero M (May 2021). Experimental Evidence for the Role of Natural Radioactivity in Influencing Viability of Commensal Microorganisms. American Journal of Immunology, 17(1), 14-24. DOI: doi.org/10.3844/ajisp.2021.14.24. This peer-reviewed article, cited as reference 2 on Information Disclosure Statement, form PTO/SB/08b, contains the same information as the article quoted above. The first article was posted on a pre-print server, bioRxiv, whereas this one was published in a peer-reviewed journal, the American Journal of Immunology.

Inventor's Expertise

Since 1989, the inventor Dr. Marco Ruggiero, MD, PhD, has accumulated a vast research experience in the area of magnetic and electromagnetic fields as they relate to biological effects and health risks. The results of his research experience are published in the peer-reviewed articles listed below as wells as in book chapters.

Hematopoietic bone marrow recovery after radiation therapy: MRI evaluation. Casamassima F, Ruggiero C, Caramella D, Tinacci E, Villari N, Ruggiero M. Blood. 1989 May 1; 73(6):1677-81

Magnetic resonance (MR) evaluation of bone marrow in vertebral bodies. Orlandini G E, Ruggiero L, Gulisano M, Ruggiero M, Villari N, Casamassima F. Arch Ital Anat Embriol. 1991 April-June; 96(2):93-100

Mitogenic signal transduction: a common target for oncogenes that induce resistance to ionizing radiations. Ruggiero M, Casamassima F, Magnelli L, Pacini S, Pierce J H, Greenberger J S, Chiarugi V P. Biochem Biophys Res Commun. 1992 183(2):652-8. doi: 10.1016/0006-291x(92)90532-p Altered metabolism of glutathione in cells transformed by oncogenes which cause resistance to ionizing radiations. Vincenzini M T, Marraccini P, Iantomasi T, Favilli F, Pacini S, Ruggiero M. FEBS Lett. 1993 Apr. 12; 320(3): 219-23. doi: 10.1016/0014-5793(93)80590-q Molecular mechanisms responsible for radioresistance in cells transformed by oncogenes involved in lung cancer. Pacini, S., Vincenzini, M. T., Marraccini, P, Iantomasi, T., Santucci, M. A., Casamassima, F. and Ruggiero, M. In: Motta, G. (Ed): "Lung Cancer. Frontiers in Science and Treatment", pp. 195-200, L. P. Graf. Publisher, 1994.

Increased formation of diacylglycerol in tumor cells that are resistant to ionizing radiations. Pacini, S., Santucci, M. A., Milano, F., Casamassima, F., Greenberger, J. S., Pierce, J. H. and Ruggiero, M. Radiat. Oncol. Invest. 2: 20-24, 1994. doi: 10.1002/roi.2970020104

Study of second messenger levels and of sugar catabolism enzyme activities in transformed cells resistant to ionizing radiations. Pacini S, Ruggiero M, Casamassima F, Santucci M A, Milano F, Ranaldi F, Vanni S, Giachetti E. Biochem Mol Biol Int. 1995 September; 37(1):81-8

Dominant oncogenes, tumor suppressors, and radiosensitivity. Chiarugi V, Magnelli L, Cinelli M, Turchetti A, Ruggiero M. Cell Mol Biol Res. 1995; 41(3):161-6

Conferring drug resistance by MDR1 gene transfection increases susceptibility to irradiation and lipid peroxidation in 3T3 cell line. Mazzanti R, Fantappie O, Fabrizio P, Pacini S, Relli P, Casamassima F, Milano F, Ruggiero M. Free Radic Biol Med. 1996; 20(4):601-6. doi: 10.1016/0891-5849(95)02063-2

Overexpression of a synthetic phosphotyrosine protein phosphatase gene increases radiosensitivity in vitro of normal and transformed murine NIH/3T3 fibroblasts. Santucci, M. A., Greenberger, J. S., Pierce, J. H., Babini, L., Barbieri, E., Pacini, S., Rigacci, S., Pazzagli, C., Berti, A., Raugei, G., and Ruggiero, M. Radiat. Oncol. Invest. 4: 1-8, 1996. doi: 10.1002/(SICI)1520-6823(1996)4:1<1::AID-ROI1>3.0.CO; 2-1

Effects of gemcitabine in normal and transformed human lung cell cultures: cytotoxicity and increase in radiation sensitivity. Pacini S, Milano F, Pinzani P, Pazzagli M, Gulisano M, Ruggiero M, Casamassima F. Tumori. 1999 November-December; 85(6):503-7

Effect of 0.2 T static magnetic field on human neurons: remodeling and inhibition of signal transduction without genome instability. Pacini S, Vannelli G B, Barni T, Ruggiero M, Sardi I, Pacini P, Gulisano M. Neurosci Lett. 1999 Jun. 4; 267(3):185-8. doi: 10.1016/s0304-3940(99)00362-6

Influence of static magnetic field on the antiproliferative effects of vitamin D on human breast cancer cells. Pacini S, Aterini S, Pacini P, Ruggiero C, Gulisano M, Ruggiero M. Oncol Res. 1999; 11(6):265-71

Nucleoside analogues as radiosensitizers in the treatment of lung cancer. Casamassima, F., Pacini, S., Panichi, M., Milano, F., Pinzani, P., Pazzagli, M., and Ruggiero, M. In "Bioluminescence and chemiluminescence: perspectives for the 21st century" Roda A., Pazzagli, M., Kricka L. J. and Stanley, P. E. Eds. John Wiley and Sons, Chichester, U.K. pp. 551-554, 1999.

Exposure to global system for mobile communication (GSM) cellular phone radiofrequency alters gene expression, proliferation, and morphology of human skin fibroblasts. Pacini S, Ruggiero M, Sardi I, Aterini S, Gulisano F, Gulisano M. Oncol Res. 2002; 13(1):19-24. doi: 10.3727/096504002108747926

Effects of 0.2 T static magnetic field on human skin fibroblasts. Pacini S, Gulisano M, Peruzzi B, Sgambati E, Gheri G, Gheri Bryk S, Vannucchi S, Polli G, Ruggiero M. Cancer Detect Prev. 2003; 27(5):327-32. doi: 10.1016/s0361-090x(03)00124-7 0.2 T magnetic field inhibits angiogenesis in chick embryo chorioallantoic membrane. Ruggiero M, Bottaro D P, Liguri G, Gulisano M, Peruzzi B, Pacini S. Bioelectromagnetics. 2004 July; 25(5):390-6. doi: 10.1002/bem.20008

Static magnetic fields, blood and genes: an intriguing relationship. Ruggiero M. Cancer Biol Ther. 2008 June; 7(6):820-1. Doi: 10.4161/cbt.7.6.6299

Electromagnetic Fields. Ruggiero M., Aterini S. (2015). In: Schwab M. (eds) Encyclopedia of Cancer. Springer, Berlin, Heidelberg. Pages 1-5.

More recently, the inventor has published scientific articles in peer-reviewed journals on the topic of biological quantum entanglement and relativistic effects as they relate to human health and disease. These articles are listed below.

Alzheimer DNA vaccine and relativistic time dilation. Ruggiero M. Journal of Neurology and Stroke 2017 7(7): 1-2. doi: 10.15406/jnsk.2017.07.00263

A Novel Approach to Klotho Aimed at Delaying and Reversing Aging. Ruggiero M. Bio Accent Open Journal HIV 2017 3(2): 0-29.

On the impact of quantum biology and relativistic time dilation in autism. Ruggiero M. and Pacini S. AIMS Molecular Science 2018 5(1): 90-95. doi: 10.3934/molsci.2018.1.90

How Quantum Biology Can Eradicate Heart Diseases. Ruggiero M. Open Journal of Cardiology and Heart Diseases 2018 1(4): 1-3. doi: 10.31031/OJCHD.2018.01.000520

Color Doppler Evaluation of Isovolumetric Relaxation Time and of Signals Arising from Axons of the Median Nerve as a Means to Evaluate Mitochondrial Functionality in the Context of Immunotherapy of Cancer and Chronic Conditions Associated with Mitochondrial Dysfunction. Pacini S. and Ruggiero M. American Journal of Immunology 2019 (15): 22-32. doi: 10.3844/ajisp.2019.22.32

Two scientific articles specifically related to this invention, published after filing the provisional patent application related to this invention are:

Ruggiero M. (2020) Experimental evidence for the role of natural radioactivity in influencing viability of commensal microorganisms. bioRxiv. doi: https://doi.org/10.1101/2020.07.21.214676

Ruggiero, M. (2021). Experimental Evidence for the Role of Natural Radioactivity in Influencing Viability of Commensal Microorganisms. American Journal of Immunology, 17(1), 14-24.

DESCRIPTION OF THE INVENTION

Examples of the Preferred Embodiments

Detailed embodiments of the present invention are disclosed herein, however, it is to be understood that the disclosed embodiments are merely exemplary of the invention, which may be embodied in various forms. Therefore, specific functional details disclosed herein are not to be interpreted as limiting, but merely as a basis for the claims and as a representative basis for teaching one skilled in the art to variously employ the present invention in virtually any appropriately detailed embodiment.

Characteristics of the materials used for manufacturing the pre-probiotic product and rationale for the use of materials with specific features.

The materials used for the manufacture of the product in this example are:
Naturally radioactive carbonated mineral water for human consumption as medium for culture/fermentation
Prebiotic microorganisms (*Arthrospira*); Proprietary blend of probiotic microorganisms.
*Equisetum arvense*.

Description, Characteristics and Rationale for the Use of Each Material

Naturally Radioactive Carbonated Mineral Water for Human Consumption as Medium for Culture/Fermentation The naturally radioactive mineral water used in this invention is carbonated and has the following chemical composition as far as minerals and radioactive isotopes are concerned.

| | |
|---|---|
| pH | 7.84 |
| $HCO_3^+$ | 223 mg/L |
| $Ca^{2+}$ | 208.0 mg/L |
| $Cl^-$ | 68 mg/L |
| $Fe^{2+}$ | >1 mg/L |
| $F^-$ | >4 mg/L |
| $Mg^{2+}$ | 53.5 mg/L |
| $Na^+$ | 42 mg/L |
| $K^+$ | 2.8 mg/L |
| $SO_4^-$ | 534.6 mg/L |
| $^{226}Ra$ | 152 mBq $l^{-1}$ |
| Uranium | 217.7 mBq $l^{-1}$ |
| Main minerals | 1,132 mg/L |

-continued

| Radioactivity from $^{226}$Ra + Uranium ($^{238}$U): | 369.7 mBq l$^{-1}$ |
| --- | --- |
| Radioactivity from Uranium: | 59% |

The rationale to choose a carbonated mineral water with these values of natural radioactivity lays in the objective of stimulating adaptogenic responses to radioactivity in radio-resistant cyanobacteria of the formula (Arthorspira, see point 7.1.2.1) that show up-regulation of a number of genes involved with DNA repair and protection against the harmful effects of electromagnetic radiations once exposed to such radiations (doi: 10.1002/mbo3.229).

In addition, charged particles emitted by the isotopes of the mineral water described above have superluminal characteristics in water and are responsible for Cherenkov radiation, a phenomenon that is well documented and whose measure is actually used to determine the amount of radioactive elements in water (Analyst, July 1993, vol. 118, pp 873-876, paper 3/00519D). Cherenkov radiation in turn, causes bioluminescence and photo-activation (doi: 10.1007/s11307-011-0489-z) that translates in the induction of photosynthesis in the cyanobacteria of the formula.

The novelty of the concept lays in the continuous and simultaneous exposure to electromagnetic radiations (from natural radioactivity), and induction of photosynthesis from Cherenkov radiation that is also due to natural radioactivity. Thus, in normal condition, that is in the absence of Cherenkov radiation, cyanobacteria down-regulate the genes presiding to photosynthesis when exposed to radiations such as gamma-rays and, at the same time, up-regulate the genes that protect them from the harmful effects of radiations (doi: 10.1002/mbo3.229). In the case described here, however, induction of photosynthesis occurs concomitantly with exposure to radiations since induction of photosynthesis is a by-product of superluminal charged particles emitted by the radioisotopes of water. As explained in other paragraphs, the process of photosynthesis is based on quantum entanglement and, therefore, up-regulation of genes involved in DNA repair and resistance to radiations and induction of photosynthesis become entangled. This leads to further entanglement between the radio-resistant cyanobacteria and the other commensal probiotics of the formula that are also exposed to the radioisotopes of water but have no photosynthetic capacity; the mechanism at the basis of living bacterial entanglement following exposure to electromagnetic fields is explained in detail in Marletto et al. (Marletto et al 2018 J. Phys. Commun. 2 101001. DOI 10.1088/2399-6528/aae224). The choice of naturally radioactive water that is also carbonated lays in the well-known concept that carbon dioxide is required for photosynthesis and such a requirement is all the more significant when the source of light is represented by the continuum spectrum of Cherenkov radiation. In addition, carbonated water shows a distinctive light scattering pattern that is very different from that of non-carbonated water. The presence of dissolved gas in the water leads to smoothing of the angular dependence of scattered light intensity, and reduction of the polydispersity degree, thus optimizing the conditions for Cherenkov radiation-induced photosynthesis (Ukr. J. Phys. Opt. 2009, vol: 10, No 1, pp 38-53). Such an optimization is due to the uniform distribution in water of the radioactive isotopes of Uranium and Radium as well as to the equally uniform distribution of the bubbles typical of carbonated water. The constant, uniform, Cherenkov radiation is scattered by the bubbles and therefore reaches the light harvesting antennae of the cyanobacteria from all possible angles at variance with a common source of light that would reach the antennae from a fixed angle.

In summary, the natural radioactivity in the carbonated mineral water evokes radio-protective responses as well as induction of photosynthesis in the cyanobacteria; through quantum entanglement, these transfer the radio-protective response to the other probiotic bacteria of the formula that are also exposed to the natural radioactivity but are not radio-resistant per se.

Prebiotic and Probiotic Microorganisms

Radio-Resistant Prebiotic Cyanobacteria: *Arthrospira*

*Arthrospira* belongs to oxygenic photosynthetic bacteria that comprises the groups Cyanobacteria and Prochloralesis. It is a filamentous bacterium that floats freely and shows tendency to aggregate; it grows preferentially in water of alkaline lakes and in regions with strong irradiation from the sun and relatively high temperature. This cyanobacterium is not pathogenic for humans and has been used as food since 16$^{th}$ century, because it has high-protein content and it is easy digestible. It is considered a prebiotic since it favors the growth of known probiotic microorganisms such as lactic acid bacteria like *Lactococcus lactis, Streptococcus thermophilus, Lactobacillus casei, Lactobacillus acidophilus,* and *Lactobacillus bulgaricus* (doi: 10.15406/jmen.2017.04.00120). All these probiotics are co-cultured with *Arthrospira* in the naturally radioactive carbonated mineral water as explained in the following paragraphs.

As a food or a food supplement, *Arthrospira* has gained increasing interest both for the general public and, more specifically, for astronauts who may be exposed to electromagnetic radiations (doi: 10.1093/ecam/nen058). In specific regard to protection against the harmful effects of electromagnetic radiations, its strong anti-oxidant and anti-inflammatory properties show potential application in human radiation protection (doi: 10.1006/bbrc.2001.5195).

As a matter of fact, *Arthrospira* is resistant to the killing effects of electromagnetic radiations and it survives exposure to gamma-rays up to 6,400 Gy with a dose rate of 527 Gy h$^{-1}$ (doi: 10.1002/mbo3.229). For reference, the median human lethal radiation dose computed from data on occupants of reinforced concrete structures in Nagasaki, Japan, is around 3 Gy (doi: 10.1097/00004032-199211000-00003). Resistance to radiations is due to a number of factors that include the presence of high level of anti-oxidants and, more importantly, induction and up-regulation of genes involved in DNA repair. Among these, of particular importance in the context of this invention are the genes of the uvr family that are involved in repair of single strand breaks (SSBs) of DNA. Although no studies are available on the direct effects of 5G on human cancer Onset and progression, a recent peer-reviewed article analyzed 94 relevant publications performing in vivo or in vitro research on this topic (high-frequency-powered base stations and other devices using 6-100 GHz, millimeter waves). According to this meta-analysis 80% of the in vivo studies showed biological responses to exposure, while 58% of the in vitro studies demonstrated effects. All the responses showed effects on all biological endpoints analyzed (doi:10.3390/ijerph16183406). In addition, a study published in May 2020 in the peer-reviewed journal "Toxicology Letters" by Authors from the Georgia Institute of Technology of the United States, McGill University of Canada, Albert Einstein College of Medicine of the United States, University of Crete of Greece, and Sechenov University of Moscow, Russia, clearly states "This article also presents evidence that the nascent 5G mobile networking technology will affect not only the skin and eyes, as commonly believed, but will have adverse systemic effects as well" (doi: 10.1016/j.toxlet.2020.01.020).

Rationale for the Use of Arthorspira

Electromagnetic radiations used for mobile telecommunication and, in particular, high frequency fields used for 5G, affect biological responses and are classified as possibly carcinogenic for humans (Non-Ionizing Radiation, Part 1: Static and Extremely Low-Frequency (ELF) Electric and Magnetic Fields. IARC Monographs on the Evaluation of Carcinogenic Risks to Humans, No. 80. IARC Working Group on the Evaluation of Carcinogenic Risks to Humans. Lyon (FR): International Agency for Research on Cancer; 2002).

The most common types of DNA damage due to these radiations are SSBs (Radiat Res. 1992 November; 132(2): 200-6).

- This damage is repaired by proteins encoded by uvr genes (doi: 10.1002/mbo3.229).
- *Arthrospira* up-regulates expression of uvr genes upon exposure to radiations (doi: 10.1002/mbo3.229).
- *Arthrospira* is known to protect against radiation sickness (Vopr Pitan. 1999; 68(1):17-19)
- *Arthrospira* protects against the damage inflicted by electromagnetic radiations through DNA repair (uvr gene up-regulation) (DOI: 10.1016/0378-4274(89)90171-9).
- Naturally radioactive carbonated mineral induces up-regulation of radiation protection genes in *Arthrospira* and Cherenkov radiation induced photosynthesis (doi: 10.1007/s11307-011-0489-z).
- Photosynthesis is based on quantum entanglement (doi: 10.1098/rspa.2016.0822).
- Electromagnetic fields such as those associated with charged particles from radioisotopes as those in mineral water induce quantum entanglement between bacteria (Marletto et al 2018 J. Phys. Commun. 2 101001. DOI 10.1088/2399-6528/aae224).
- Quantum entanglement and transfer of resistance to radiation between living organisms occurs in water (doi: 10.1177/1559325817750067).

Ergo

*Arthrospira*, a prebiotic bacterium already known to protect from radiation sickness, once exposed to (cultured in) naturally radioactive mineral water, activates mechanisms for DNA protection (uvr genes) that are known to protect against SSBs, and transfers such a protection to probiotic microorganisms co-cultured in the same medium that in turn transfer such a protection to human cells through phages (as explained in the following paragraphs).

Example of Blend of Probiotic Microorganisms

Probiotic microorganism are cultured together with *Arthrospira* in naturally radioactive carbonated mineral water. The complete culture medium is described in the following paragraphs. The probiotic microorganisms are members of the families of Streptococcaceae, Lactobacillaceae, Leuconostocaceae, Bifidobacteriaceae, and Thermaceae. The blend contains also lyophilized kefir grains that are characterized by a complex composition.

Consistent with such a biodiversity, it was recently demonstrated that a typical kefir product contains hundreds of different microbial species and this is deemed responsible for the known health-supporting properties of kefirs that range from modulating the immune system to fighting carcinogenesis and allergies, from favoring wound healing to regulating cholesterol metabolism and blood pressure (doi: 10.1371/journal.pone.0212045).

The probiotic blend used in this invention contains phages and plasmid DNA. The precise composition of the blend in terms of strains, plasmids and phages is assessed by a microbiome array (Axiom Microbiome Array). This is a chip covered in short DNA sequences that are specific to certain target organisms and a total of approximately 12,000 species are included. For each target organism, the software looks at the ratio of probes that successfully bound to their target (Probes Observed) to the total number that could potentially bind (Probes Expected), and uses this to calculate the Initial Score, which is proportional to the likelihood of the target existing in the tested sample. Once the software identifies the target that it deems most likely to be present in the actual sample, the probes that correspond to the chosen target are removed and the process is repeated until adding new species no longer adds explanatory power to the software's model of the composition of the sample. The products of this iterative analysis are called Iterations. Probes are considered positive when presenting signal intensity higher than 99th percentile of the random control probe intensities with a percentage of more than 20% of target-specific probes detected. In other words, a target organism is considered present in the sample when the percentage of observed probes is greater than 20% of the expected probes. The array is capable of accurately detecting members of mock microbial communities used for testing, achieving 100% accuracy in species identification; the specificity of the array yields precious information for diagnosis and surveillance of pathogens in food matrices, at the same time providing strain level detections since the array was designed to detect specific genomic regions of the sequences represented on the chip.

Table 1, shows the plasmid composition of the probiotic blend. The array provided 48 iterations, each one corresponding to an unique target. The targets are ordered in descending sequence with those showing the highest percentage of observed probes at the top of the list. Although the assay is not quantitative, it can be deduced that higher percentages correspond to higher number of copies (doi: 10.1371/journal.pone.0212045). Lc: *Lactococcus*. Lb: *Lactobacillus*.

Table 2, shows the targets corresponding to Lactobacilli present in the blend. The array identified the following *Lactobacillus* strains: *paracasei, casei, helveticus, kefiranofaciens, plantarum, gallinarum, delbrueckii, rhamnosus, salivarium, acidophilus, farraginis,* and *antri*. The substrains are listed in Table 2.

Table 3 shows the targets corresponding to *Lactococcus lactis* strains and substrains present in the blend. The substrains identified by the array are listed in the Table.

TABLE 1

List of targets corresponding to plasmids

| Target description | Conditional Score | Initial Score | Probes Expected | Probes Observed | % |
|---|---|---|---|---|---|
| Lc. lactis subsp. lactis KLDS 4.0325 plasmid 2 | 5.99 | 40.75 | 13 | 11 | 84.61 |
| S. thermophilus LMD-9 plasmid 2 | 155.25 | 155.25 | 57 | 43 | 75.43 |
| Lb. paracasei subsp. paracasei JCM 8130 plasmid pLBPC-2 DNA | 66.02 | 197.87 | 73 | 55 | 75.34 |
| Lc. lactis lactis bv. diacetylactis DPC220 plasmid pAH82 | 92.13 | 170.15 | 63 | 47 | 74.6 |

TABLE 1-continued

List of targets corresponding to plasmids

| Target description | Conditional Score | Initial Score | Probes Expected | Probes Observed | % |
|---|---|---|---|---|---|
| *Le. mesenteroides mesenteroides* FR52 plasmid pFR18 | 63.49 | 90.57 | 36 | 26 | 72.22 |
| *Lc. lactis cremoris* HP plasmid pHP003 | 12.45 | 103.24 | 41 | 29 | 70.73 |
| *Lc. lactis* plasmid pSK11B | 128.09 | 163.05 | 67 | 47 | 70.14 |
| *S. thermophilus* SMQ-173 plasmid pSMQ173b | 128.2 | 128.2 | 53 | 37 | 69.81 |
| *Lc. lactis* subsp. *cremoris* A76 plasmid pQA504 | 136.59 | 136.59 | 56 | 39 | 69.64 |
| *S. thermophilus* LMD-9 plasmid 1 | 123.93 | 123.93 | 52 | 36 | 69.23 |
| *Lc. lactis* IL964 plasmid pIL105 | 106.65 | 126.21 | 52 | 36 | 69.23 |
| *Lc. lactis* IL964 plasmid pIL105 | 103.11 | 126.21 | 52 | 36 | 69.23 |
| *Lc. lactis* subsp. *cremoris* UC509.9 plasmid pCIS2 | 46.14 | 57.96 | 25 | 17 | 68.0 |
| *Lc. lactis* DCH-4 plasmid pSRQ700 | 72.45 | 150.87 | 65 | 44 | 67.69 |
| *Lb. plantarum* subsp. *plantarum* P-8 plasmid LBPp2 | 2.57 | 198.2 | 88 | 58 | 65.9 |
| *Lc. lactis* subsp. *cremoris* SK111plasmid 5 | 115.99 | 147.8 | 67 | 44 | 65.67 |
| *Lb. plantarum* subsp. *plantarum* P-8 plasmid LBPp5 | 2.66 | 153.2 | 69 | 45 | 65.21 |
| *Lc. lactis* subsp. *cremoris* SK11 plasmid 2 | 90.17 | 117.35 | 54 | 35 | 64.81 |
| *Lc. lactis cremoris* NIZO B40 plasmid pNZ4000 | 14.74 | 228.55 | 106 | 68 | 64.15 |
| *Le. citreum* KM20 plasmid pLCK1 | 17.86 | 159.68 | 76 | 48 | 63.15 |
| *Lc. lactis* subsp. *lactis* bv. *diacetylactis* plasmid pVF18 | 93.2 | 132.29 | 62 | 39 | 62.9 |
| *Lc. lactis* subsp. *cremoris* UC509.9 plasmid pCIS5 | 81.58 | 116.52 | 56 | 35 | 62.5 |
| *Lb. buchneri* CD034 plasmid pCD034-3 | 94.91 | 140.4 | 69 | 43 | 62.31 |
| *Lc. lactis cremoris Cremoris* Wg2 plasmid pWVO2 | 26.9 | 61.67 | 31 | 19 | 61.29 |
| *Lc. lactis* subsp. *lactis* plasmid pIL1 | 0.83 | 54.63 | 32 | 18 | 56.25 |
| *Lb. casei* str. Zhang plasmid plca36 | 100.3 | 158.65 | 96 | 53 | 55.2 |
| *Lc. lactis* subsp. *lactis* strain MJC15 plasmid pCD4 | 52.85 | 56.57 | 35 | 19 | 54.28 |
| *Lc. lactis* plasmid pWC1 | 38.57 | 50.32 | 30 | 16 | 53.33 |
| *Lc. lactis* subsp. *lactis* plasmid pIL3 | 15.13 | 110.35 | 69 | 36 | 52.17 |
| *Lc. lactis* plasmid pND324 | 0.47 | 36.11 | 23 | 12 | 52.17 |
| *Lb. gasseri* plasmid pLgLA39 | 93.5 | 149.57 | 101 | 52 | 51.48 |
| *Lb. salivarius* CECT 5713 plasmid pHN1 | 73.16 | 124.25 | 88 | 44 | 50.0 |
| *S. macedonicus* ACA-DC 198 plasmid pSMA198 | 31.1 | 69.82 | 48 | 24 | 50.0 |
| *Lb. salivarius* CECT 5713 plasmid pHN1 | 30.61 | 124.25 | 88 | 44 | 50.0 |
| *Lc. lactis* subsp. *cremoris* SK11 plasmid 1 | 75.05 | 94.81 | 67 | 33 | 49.25 |
| *Lb. salivarius* UCC118 plasmid pSF118-44 | 71.3 | 118.83 | 90 | 43 | 47.77 |
| *Lc. lactis* subsp. *lactis* CV56 plasmid pCV56C | 3.87 | 86.4 | 65 | 31 | 47.69 |
| *S. thermophilus* ST135 plasmid pER35 | 78.45 | 102.38 | 84 | 38 | 45.23 |
| *Lb. helveticus* R0052 plasmid pIR52-1 | 35.13 | 74.41 | 62 | 28 | 45.16 |
| *Lc. lactis* subsp. *lactis* KF147 plasmid pKF147A | 45.99 | 93.75 | 93 | 38 | 40.86 |
| *Lb. paracasei* subsp. *paracasei* plasmid pCD01 | 12.17 | 70.63 | 88 | 34 | 38.63 |
| *P. damnosus* plasmid pF8801 | 62.73 | 62.73 | 86 | 31 | 36.04 |
| *Lb. buchneri* CD034 plasmid pCD034-1 | 63.05 | 63.05 | 100 | 34 | 34.0 |
| *Lc. lactis* plasmid pKL001 | 6.34 | 25.25 | 51 | 16 | 31.37 |
| *Lb. salivarius* CECT 5713 plasmid pHN2 | 0.16 | 23.76 | 69 | 20 | 28.98 |
| *Lb. paracasei* N1115 plasmid | 21.36 | 21.36 | 70 | 20 | 28.57 |
| *Le. mesenteroides* subsp. *mesenteroides* cryptic plasmid pTXL1 | 7.63 | 7.63 | 63 | 15 | 23.8 |
| *Lb. brevis* ATCC 367 plasmid 1 | 3.44 | 3.44 | 61 | 14 | 22.95 |

End of Table 1

TABLE 2

List of targets corresponding to Lactobacilli

Target Description

*Lactobacillus paracasei* subsp. *paracasei* Lpp43 draft (205 frags)
*Lactobacillus paracasei* subsp. *paracasei* Lpp221 draft (265 frags)
*Lactobacillus paracasei* subsp. *paracasei* Lpp228 draft (188 frags)
*Lactobacillus paracasei* subsp. *paracasei* Lpp189 draft (295 frags)
*Lactobacillus paracasei* subsp. *paracasei* Lpp226 draft (131 frags)
*Lactobacillus paracasei* subsp. *paracasei* Lpp74 draft (190 frags)
*Lactobacillus paracasei* subsp. *paracasei* Lpp17 draft (131 frags)
*Lactobacillus paracasei* subsp. *paracasei* Lpp219 draft (238 frags)
*Lactobacillus paracasei* subsp. *paracasei* Lpp223 draft (168 frags)
*Lactobacillus paracasei* subsp. *paracasei* Lpp225 draft (74 frags)
*Lactobacillus paracasei* subsp. *paracasei* Lpp229 draft (317 frags)
*Lactobacillus paracasei* subsp. *paracasei* Lpp125 draft (192 frags)
*Lactobacillus paracasei* subsp. *paracasei* Lpp49 draft (109 frags)
*Lactobacillus paracasei* subsp. *paracasei* Lpp227 draft (596 frags)
*Lactobacillus paracasei* subsp. *paracasei* CNCM I-4648 draft (852 frags)
*Lactobacillus paracasei* subsp. *paracasei* CNCM I-4270 draft (461 frags)
*Lactobacillus paracasei* subsp. *paracasei* CNCM I-2877 draft (481 frags)
*Lactobacillus paracasei* subsp. *paracasei* Lpp46 draft (90 frags)
*Lactobacillus paracasei* subsp. *paracasei* Lpp70 draft (474 frags)
*Lactobacillus paracasei* subsp. *paracasei* Lpp120 draft (201 frags)

TABLE 2-continued

List of targets corresponding to Lactobacilli

Target Description

*Lactobacillus paracasei* subsp. *paracasei* Lpp22 draft (270 frags)
*Lactobacillus paracasei* subsp. *paracasei* 8700:2 draft (90 frags)
*Lactobacillus paracasei* subsp. *paracasei* Lpp126 draft (1355 frags)
*Lactobacillus paracasei* subsp. *paracasei* Lpp7 draft (611 frags)
*Lactobacillus paracasei* subsp. *paracasei* Lpp37 draft (264 frags)
*Lactobacillus paracasei* COM0101 draft (184 frags)
*Lactobacillus casei* CRF28 draft (57 frags)
*Lactobacillus casei* M36 draft (78 frags)
*Lactobacillus casei* A2-362 draft (167 frags)
*Lactobacillus casei* Lpc-37 draft (150 frags)
*Lactobacillus casei* T71499 draft (55 frags)
*Lactobacillus casei* A2-362 draft (164 frags)
*Lactobacillus casei* LcA draft (18 frags)
*Lactobacillus casei* LcY draft (14 frags)
*Lactobacillus casei* UCD174 draft (116 frags)
*Lactobacillus casei* 21/1 draft (75 frags)
*Lactobacillus casei* BL23 chromosome
*Lactobacillus casei* LC2W chromosome
*Lactobacillus casei* BD-II chromosome
*Lactobacillus casei* W56
*Lactobacillus casei* Lc-10 draft (76 frags)
*Lactobacillus casei* 5b draft (91 frags)
*Lactobacillus casei* UW1 draft (143 frags)
*Lactobacillus casei* 32G draft (42 frags)
*Lactobacillus helveticus* CNRZ32
*Lactobacillus helveticus* MTCC 5463 draft (593 frags)
*Lactobacillus helveticus* CIRM-BIA 104 draft (234 frags)
*Lactobacillus helveticus* CIRM-BIA 953 draft (203 frags)
*Lactobacillus helveticus* CIRM-BIA 103 draft (222 frags)
*Lactobacillus helveticus* CIRM-BIA 101 draft (213 frags)
*Lactobacillus helveticus* CIRM-BIA 951 draft (179 frags)
*Lactobacillus helveticus* DPC 4571
*Lactobacillus helveticus* R0052 chromosome
*Lactobacillus helveticus* H10 chromosome
*Lactobacillus helveticus* DSM 20075 draft (235 frags)
*Lactobacillus helveticus* H9
*Lactobacillus kefiranofaciens* subsp. *kefiranofaciens* JCM 6985 draft (123 frags)
*Lactobacillus kefiranofaciens* ZW3 chromosome
*Lactobacillus plantarum* UCMA 3037 draft (92 frags)
*Lactobacillus plantarum* strain AG30 draft (48 frags)
*Lactobacillus plantarum* IPLA88 draft (208 frags)
*Lactobacillus plantarum* 2025 draft (595 frags)
*Lactobacillus plantarum* 19L3 draft (241 frags)
*Lactobacillus plantarum* 2165 draft (192 frags)
*Lactobacillus plantarum* 16
*Lactobacillus plantarum* ZJ316
*Lactobacillus plantarum* 4_3 draft (105 frags)
*Lactobacillus plantarum* WCFS1
*Lactobacillus plantarum* WJL draft (102 frags)
*Lactobacillus plantarum* strain Lp90 draft (33 frags)
*Lactobacillus plantarum* JDM1
*Lactobacillus plantarum* LP91 draft (145 frags)
*Lactobacillus plantarum* strain DmCS_001 draft (83 frags)
*Lactobacillus plantarum* subsp. *plantarum* P-8
*Lactobacillus plantarum* subsp. *plantarum* NC8 draft (10 frags)
*Lactobacillus plantarum* subsp. *plantarum* strain wikim18 draft (323 frags)
*Lactobacillus plantarum* subsp. *plantarum* ST-III chromosome
*Lactobacillus plantarum* subsp. *plantarum* ATCC 14917 draft (36 frags)
*Lactobacillus plantarum* subsp. *plantarum* JCM 1149 draft (39 frags)
*Lactobacillus gallinarum* JCM 2011 draft (74 frags)
*Lactobacillus delbrueckii* subsp. *lactis* DSM 20072 draft (167 frags)
*Lactobacillus delbrueckii* subsp. *lactis* draft (23 frags)
*Lactobacillus delbrueckii* subsp. *lactis* draft (75 frags)
*Lactobacillus delbrueckii* subsp. *lactis* CRL581 draft (231 frags)
*Lactobacillus delbrueckii* subsp. *lactis*
*Lactobacillus delbrueckii* subsp. *lactis* draft (75 frags)
*Lactobacillus delbrueckii* subsp. *bulgaricus* draft (14 frags)
*Lactobacillus delbrueckii* subsp. *bulgaricus* CNCM I-1519 draft (70 frags)
*Lactobacillus delbrueckii* subsp. *bulgaricus* CNCM I-1632 draft (69 frags)
*Lactobacillus delbrueckii* subsp. *bulgaricus* ND02 chromosome
*Lactobacillus delbrueckii* subsp. *bulgaricus* ATCC 11842 chromosome
*Lactobacillus delbrueckii* subsp. *bulgaricus* ATCC BAA-365 chromosome
*Lactobacillus delbrueckii* subsp. *bulgaricus* 2038 chromosome
*Lactobacillus delbrueckii* ZN7a-9 draft (75 frags)
*Lactobacillus rhamnosus* CRL1505 draft (218 frags)
*Lactobacillus rhamnosus* ATCC 8530 chromosome TABLE 2-continued List of targets corresponding to Lactobacilli Target Description

*Lactobacillus rhamnosus* HMP0056 *Lactobacillus rhamnosus* LMS2-1 draft (162 frags)
*Lactobacillus rhamnosus* HMP0056 *Lactobacillus rhamnosus* LMS2-1 draft (116 frags)
*Lactobacillus rhamnosus* CRL1505 draft (218 frags)
*Lactobacillus rhamnosus* strain 24 draft (90 frags)
*Lactobacillus rhamnosus* 2166 draft (84 frags)
*Lactobacillus rhamnosus* LRHMDP3 draft (47 frags)
*Lactobacillus rhamnosus* LRHMDP2 draft (50 frags)
*Lactobacillus rhamnosus* 51B draft (21 frags)
*Lactobacillus salivarius* ACS-116-V-Col5a draft (154 frags)
*Lactobacillus salivarius* cp400 draft (89 frags)
*Lactobacillus salivarius* NIAS840 draft (4 frags)
*Lactobacillus salivarius* ATCC 11741 draft (54 frags)
*Lactobacillus salivarius* cp400 draft (89 frags)
*Lactobacillus salivarius* strain JCM1046
*Lactobacillus salivarius* GJ-24 draft (11 frags)
*Lactobacillus salivarius* CECT 5713 chromosome
*Lactobacillus acidophilus* JCM 1132 draft (26 frags)
*Lactobacillus acidophilus* CIRM-BIA 445 draft (41 frags)
*Lactobacillus acidophilus* NCFM chromosome
*Lactobacillus acidophilus* CIP 76.13 draft (55 frags)
*Lactobacillus acidophilus* DSM 9126 draft (45 frags)
*Lactobacillus acidophilus* ATCC 4796 draft (69 frags)
*Lactobacillus acidophilus* La-14
*Lactobacillus farraginis* JCM 14108 draft (129 frags)
*Lactobacillus antri* DSM 16041 draft (76 frags)

End of Table 2

TABLE 3

List of targets corresponding to Lactococci

Target Description

*Lactococcus lactis* subsp. *lactis* bv. *diacetylactis* str. LD61 draft (132 frags)
*Lactococcus lactis* subsp. *lactis* bv. *diacetylactis* str. TIFN4 draft (182 frags)
*Lactococcus lactis* subsp. *lactis* bv. *diacetylactis* str. TIFN2 draft (143 frags)
*Lactococcus lactis* subsp. *lactis* bv. *diacetylactis* strain GL2 draft (22 frags)
*Lactococcus lactis* subsp. *cremoris* CNCM I-1631 draft (131 frags)
*Lactococcus lactis* subsp. *cremoris* TIFN3 draft (412 frags)
*Lactococcus lactis* subsp. *cremoris* GE214 draft (243 frags)
*Lactococcus lactis* subsp. *cremoris* TIFN1 draft (291 frags)
*Lactococcus lactis* subsp. *cremoris* TIFN7 draft (370 frags)
*Lactococcus lactis* subsp. *cremoris* TIFN5 draft (646 frags)
*Lactococcus lactis* subsp. *cremoris* TIFN6 draft (748 frags)
*Lactococcus lactis* subsp. *cremoris* HP draft (213 frags)
*Lactococcus lactis* subsp. *cremoris* MG1363 chromosome
*Lactococcus lactis* subsp. *cremoris* NZ9000 chromosome
*Lactococcus lactis* subsp. *cremoris* A76 chromosome
*Lactococcus lactis* subsp. *lactis* Dephy 1 draft (62 frags)
*Lactococcus lactis* subsp. *lactis* A12 draft (42 frags)
*Lactococcus lactis* subsp. *lactis* YF11 draft (71 frags)
*Lactococcus lactis* subsp. *lactis* JCM 5805 = NBRC 100933 draft (88 frags)
*Lactococcus lactis* subsp. *lactis* CV56 chromosome
*Lactococcus lactis* subsp. *lactis* KLDS 4.0325
*Lactococcus lactis* subsp. *lactis* Il1403 chromosome
*Lactococcus lactis* subsp. *lactis* KF147 chromosome
*Lactococcus lactis* subsp. *lactis* strain 511
*Lactococcus lactis* subsp. *lactis* NCDO 2118
*Lactococcus lactis* subsp. *lactis* NCDO 2118 draft (509 frags)
*Lactococcus lactis* subsp. *lactis* IO-1 DNA End of Table 3

Table 4, shows the phage composition of the blend. The array provided 27 iterations corresponding to unique Siphoviridae phage targets. The phages are ordered in descending sequence with those showing the highest percentage of observed probes at the top of the list.

TABLE 4

| Species | Target Description | Conditional Score | Initial Score | Probes Expected | Probes Observed | % |
|---|---|---|---|---|---|---|
| *Lactococcus* phage BM13 | *Lactococcus* phage BM13 | 175.56 | 175.56 | 67 | 49 | 73.13 |
| *Lactococcus* phage P335 sensu lato | *Lactococcus* phage Q33 | 158.28 | 158.28 | 69 | 46 | 66.66 |
| *Leuconostoc* phage phiLN03 | *Leuconostoc* phage phiLN03 | 187.97 | 187.97 | 93 | 57 | 61.29 |
| *Leuconostoc* phage phiLN04 | *Leuconostoc* phage phiLN04 | 180.09 | 180.09 | 91 | 55 | 60.43 |
| *Leuconostoc* phage phiLN12 | *Leuconostoc* phage phiLN12 | 194 | 194 | 100 | 60 | 60 |
| *Lactococcus* phage ul36 | *Lactococcus* phage ul36 | 115.08 | 115.08 | 60 | 36 | 60 |
| *Lactococcus* phage ul36 | *Lactococcus* phage ul36.k1 | 111.18 | 111.18 | 59 | 35 | 59.32 |
| *Lactococcus* phage Tuc2009 | *Lactococcus* phage Tuc2009 | 115.2 | 115.2 | 65 | 37 | 56.92 |
| *Streptococcus* phage TP-778L | *Streptococcus* phage TP-778L complete genome | 129.83 | 129.83 | 74 | 42 | 56.75 |
| *Lactococcus* phage ul36 | *Lactococcus* phage ul36.k1t1 | 17.94 | 56.8 | 34 | 19 | 55.88 |
| *Lactococcus* phage phiLC3 | *Lactococcus* phage phiLC3 | 88.77 | 104.49 | 61 | 34 | 55.73 |
| *Leuconostoc* phage phiLN6B | *Leuconostoc* phage phiLN6B | 160.05 | 160.05 | 92 | 51 | 55.43 |

TABLE 4-continued

| Species | Target Description | Conditional Score | Initial Score | Probes Expected | Probes Observed | % |
|---|---|---|---|---|---|---|
| Lactococcus phage 936 sensu lato | Lactococcus phage fd13 | 137.07 | 137.07 | 94 | 48 | 51.06 |
| Streptococcus phage 2972 | Streptococcus phage 2972 | 128.48 | 128.48 | 97 | 47 | 48.45 |
| Lactococcus phage 936 sensu lato | Lactococcus lactis phage 645 | 92.93 | 104.19 | 80 | 38 | 47.5 |
| Streptococcus phage DT1 | Streptococcus phage DT1 | 72.49 | 92.07 | 75 | 35 | 46.66 |
| Lactococcus phage 340 | Lactococcus phage 340 | 108.36 | 119.62 | 95 | 44 | 46.31 |
| Lactococcus phage jm2 | Lactococcus phage jm2 | 29.41 | 76.21 | 68 | 30 | 44.11 |
| Lactococcus phage r1t | Lactococcus phage r1t | 26.01 | 64.17 | 60 | 26 | 43.33 |
| Lactococcus phage 936 sensu lato | Lactococcus phage CB19 | 54.42 | 96.69 | 95 | 40 | 42.10 |
| Lactococcus phage jm3 | Lactococcus phage jm3 | 16.17 | 70.86 | 74 | 30 | 40.54 |
| Streptococcus phage Sfi11 | Streptococcus phage Sfi11 | 18.39 | 86.09 | 94 | 38 | 40.42 |
| Lactococcus phage 936 sensu lato | Lactococcus phage CB14 | 50.96 | 81.97 | 91 | 36 | 39.56 |
| Streptococcus phage Sfi19 | Streptococcus phage Sfi19 | 57.49 | 65.53 | 86 | 32 | 37.20 |
| Lactococcus phage TP901-1 | Lactococcus phage TP901-1 | 10.84 | 33.58 | 57 | 19 | 33.33 |
| Lactococcus phage 936 sensu lato | Lactococcus phage 712 | 1.06 | 39.1 | 70 | 23 | 32.85 |
| Lactococcus phage BK5-T | Lactococcus phage BK5-T | 12.91 | 12.91 | 61 | 16 | 26.22 |

End of Table 4

Rationale for the Use of the Probiotic Blend Here Described as an Example

The human microbiota is negatively affected by electromagnetic radiations of mobile telecommunication (doi: 10.1007/s12275-017-7208-7). This probiotic blend contains the highest number of live probiotic microorganisms; there are no other probiotic blends with such a high biodiversity. Such a biodiversity reproduces the complexity of the human microbiota, thus reconstituting an organ that is essential for human health The proprietary probiotic blend contains plasmids that are known to transfer biological information between bacteria (Madridge J Immunol. 2019; 3(2): 100-108. doi: 10.18689/mjim-1000123). This feature is essential for exchanging biological information pertaining to radiation protection.

The proprietary probiotic blend contains phages that are known to stimulate immunity, repair DNA and transfer biological information to human cells (J Neurol Stroke. 2020; 10(2):80-90. DOI: 10.15406/jnsk.2020.10.00416). Independent of the route of administration, phages enter the bloodstream and tissues and interact with immune cells (macrophages, T-cells, Natural Killer cells, B-cells, granulocytes) (doi: 10.3390/v11010010).

Phages show anti-inflammatory properties and inhibit excessive reactive oxygen species production (Front. Immunol. 8:1783. doi: 10.3389/fimmu.2017.01783). Excessive reactive oxygen species production is one of the consequences of exposure to electromagnetic radiations and it is responsible for damage to DNA, proteins and cell structures (doi: 10.3109/15368378.2011.587930; doi: 10.1155/2012/740280).

The proprietary probiotic blend contains naturally formed Gc protein-derived Macrophage Activating Factor (Gc-MAF), a cytokine that stimulates/rebalances the immune system and in the probiotic blend is 100 fold more active than chemically-obtained GcMAF (American Journal of Immunology, 16(1), 8-18).

Optimization of macrophage function is of utmost importance in counteracting the harmful effects of electromagnetic radiations used in mobile telecommunication since exposure to these electromagnetic radiations provokes macrophage dysfunction (doi: 10.1080/09553002.2018.1465610) that contributes to immune system disturbances (doi: 10.1016/j.pathophys.2009.03.004) that, in turn, contributes to adverse health effects of 5G mobile networking technology under real-life conditions (Toxicology Letters Volume 323, 1 May 2020, Pages 35-40).

Electromagnetic radiations of the type used for mobile telecommunication cause excessive formation of reactive oxygen species and leads to death (apoptosis) of human blood macrophages (doi: 10.1155/2012/740280). The simultaneous presence of phages, that inhibit excessive reactive oxygen species (Front. Immunol. 8:1783. doi: 10.3389/fimmu.2017.01783), and GcMAF, that stimulates human blood macrophages (doi: 10.5301/jn.5000035), prevents these harmful effects of electromagnetic radiations on macrophages that are cells whose function is essential for the immune system.

The simultaneous presence of phages and GcMAF leads to optimization of immune system function at the same time preventing inflammation (Front. Immunol. 8:1783. doi: 10.3389/fimmu.2017.01783), a threatening pathologic feature that accompanies dysregulated immune responses to mobile telecommunication electromagnetic radiations (doi: 10.1590/S1677-5538.IBJU.2014.04.11).

Co-cultivation of *Arthrospira* and the probiotic blend in the same aqueous medium allows exchange of biological information through horizontal gene transfer and quantum entanglement as specifically demonstrated for protective responses to radiations (doi: 10.1177/1559325817750067).

Equisetum arvense

*Equisetum arvense* (field horsetail) is a perennial plant from the family of Equisetaceae. It shows a yellowish non-photosynthetic fertile stem that bears spores and is produced in early spring. In late spring and up to late autumn, the green, photosynthetic, heavily branched sterile stems are produced. The sterile stem contains the biologically active part of the plant (*Equiseti herba*) that is mentioned in European Pharmacopeia. Flavonoids, phenolic acids, alkaloids, phytosterols, tannins, and triterpenoids are among the most widely known phytochemical compounds of *Equisetum arvense*. Several scientific articles have described different biological effects of *Equisetum arvense* such as anti-oxidant, anti-inflammatory, anti-bacterial, anti-fungal, blood vessel relaxant, neuro- and cardio-protective, and anti-proliferative properties (Oxidative Medicine and Cellular Longevity Volume 2018, Article ID 3060525). The anti-cancer properties of *Equisetum arvense* are so well-documented that a recent scientific articles published in 2020 states "[*Equisetum arvense*] may serve as an alternative anticancer agent for the treatment of pancreatic carcinoma with no or least side effects to the patient" (Saudi Journal of Biological Sciences Volume 27, Issue 5, May 2020, Pages 1260-1264). Also the anti-inflammatory properties of the plant are well documented and the mechanism of action for the anti-inflammatory effect is based on modulation of interleukins and interferon (doi: 10.1055/s-0043-123075).

The rationale for using *Equisetum arvense* in the formula described here as an example of what can be manufactured following the processes and methods that constitute this invention is based on two properties of the plant     Its anti-oxidant properties that counteract oxidative stress caused by electromagnetic radiations, thus synergizing with *Arthrospira* and with phages of the proprietary probiotic blend resulting in inhibition of excessive reactive oxygen species formation.

The high content of silica that is arranged in surface fractals in the stem and leaf of *Equisetum*.

Silica from *Equisetum arvense*, i.e. from natural origin, plays a fundamental role in the formula described in this invention as it favors horizontal gene transfer between radio-resistant *Arthrospira* and the bacteria of the proprietary probiotic blend. A number of studies have demonstrated that adsorption to minerals such as silica and silicated increases DNA longevity and stability in the environment. Such DNA-mineral associations can play the role of pools of genes that can be stored across time, an essential feature in a formula designed to withstand the noxious effects of electromagnetic radiations. More importantly for the transfer of biological information is the fact that DNA associated with silica is available for incorporation into organisms different from those where DNA originated through the process of horizontal gene transfer. The complex silica-DNA hold an unrecognized potential for successfully transferring genetic material across environments and timescales to distant organisms up to the point that it has been hypothesizes that this process has significantly influenced the evolution of life on Earth (doi: 10.3389/fmicb.2018.02217). Interestingly, *Equisetum* is considered a "living fossil", since it is the only living genus of the entire subclass Equisetidae, a class that was widely represented in the late Paleozoic forests and survived the largest extinction event in the history of Earth, the Permian-Triassic extinction event.

In the context of the formula of the product, *Equisetum arvense* serves the purpose of reproducing the condition that are believed to be present at the beginning of the life on Earth, when nucleic acids bound to minerals such as silica and silicates, and were thus able to maintain, transfer, and propagate the primeval biological information. More precisely, silica favors exchange of information between radio-resistant *Arthrospira* and the bacteria of the proprietary probiotic blend. Such an optimization of the exchange of biological information mediated by silica occurs at the classical biochemical level through horizontal gene transfer as well as at the quantum level. It has been demonstrated that DNA self-assembles in network structures on silica surfaces in such a way that it can be used for quantum computation (Superlattices and Microstructures. Volume 32, Issues 4-6, October-December 2002, Pages 215-220), and it has also been demonstrated that quantum entanglement synchronizes DNA strand breakage across relatively large distances by enzymes that recognize specific sequences. Such a quantum entanglement, that in the case of this formula is amplified by silica, explains the observed persistent effects of enzymes that interact with DNA across longer spatial separations, a phenomenon that cannot be explained in terms of classical biochemistry (doi:10.1016/j.jtbi.2015.11.018).

In addition, silica serves the purpose of absorbing phages, thereby enhancing their effectiveness in transferring the information to other bacteria as well as to human cells. It has been demonstrated that phages are active while adsorbed on the surface of silica particles and the number of active phages bound to the silica is enhanced by the presence of ionic surfaces, with greater surface charge—to a maximum—correlating with greater concentration of adsorbed phages (doi: 10.1016/j.biomaterials.2009.11.029). In the formula described in this document, the ionic surface are represented by the phenolic acids of *Equisetum* and the simultaneous presence of silica and phenolic acids leads to synergism as far as phage absorption is concerned.

Explanation of the Molecular Mechanisms of Action at the Basis of the Processes and Methods that Constitute this Invention The molecular mechanisms explaining the functioning of the present invention are described in detail in a recent article published by the inventor after having filed the relative provisional patent application (Ruggiero M. (2020) bioRxiv. doi.org/10.1101/2020.07.21.214676). In short, the transfers of information that are responsible for the efficacy of the present invention are based on the homologies of amino acid sequence and function of the genes belonging to the family of uvr. The UvrABC repair system catalyzes the recognition and processing of DNA lesions. A damage recognition complex composed of 2 UvrA and 2 UvrB subunits scans DNA for abnormalities. Upon binding of the UvrA2B2 complex to a putative damaged site, the DNA wraps around one UvrB monomer. DNA wrap is dependent on, ATP binding by UvrB and causes local melting of the DNA helix, facilitating insertion of UvrB beta-hairpin between the DNA strands. Then UvrB probes one DNA strand for the presence of a lesion. If a lesion is found the UvrA subunits dissociate and the UvrB-DNA pre-incision complex is formed. This complex is subsequently bound by UvrC and the second UvrB is released. If no lesion is found, the DNA wraps around the other UvrB subunit that will check the other strand for damage.

The inventor discovered that proteins coded for by uvr genes of Arthospira and *Lactococcus lactis* subsp. *lactis* share significant homologies that are responsible for the transfer of information as described in Ruggiero M. (2020) bioRxiv. doi.org/10.1101/2020.07.21.214676. The similarities and homologies explain the transfer of information between *Arthrospira* and one of the constituents of the proprietary probiotic blend. The following original observations by the inventor explain the transfer of information to human cells through the intermediary that is constituted by *Lactococcus* phage u136.

The complete genomic sequence of the *Lactococcus lactis* phage u136 belonging to P335 lactococcal phage species was determined and analyzed in 2002 (doi: 10.1006/viro.2002.1401). The genomic sequence of this lactococcal phage contained 36,798 base pairs with an overall G+C content of 35.8 mol %. Fifty-nine open reading frames (ORFs) of more than 40 codons were found. N-terminal sequencing of phage structural proteins as well as bioinformatic analysis led to the attribution of a function to 24 of these ORFs (41%). Among these, of particular importance in the context of this invention is the ORF designated ORF252 (Q9MC33). This protein is a viral ancestor of the human protein RAD52 that is essential for DNA repair, resistance to the harmful effects of electromagnetic radiations, genomic stability and, cancer prevention (doi: 10.15406/jnsk.2020.10.00416). Purified ORF252 binds single-stranded DNA preferentially over double-stranded DNA and promotes the renaturation of long complementary single-stranded DNAs in the context of DNA repair. Interestingly, ORF252 is able to self-assemble even in the absence of DNA with the formation of toroidal structures (doi: 10.1016/j.cub.2008.06.071). This feature of ORF252 is interesting in the context of this invention, with particular reference to DNA repair, in particular, if it is compared to the self-assembly of a major protein contributing to human genome stability, the tumor suppressor protein p53, "the guardian of the—human—genome" (doi: 10.1016/j.pharmthera.2017.03.013). It was demonstrated that four p53 molecules need DNA to self-assemble on two half-sites of the polynucleotide to form a tetramer that consists of a dimer of dimers whose stabilization is assured by protein-protein and DNA base-stacking interactions (Mol Cell. 2006 Jun. 23; 22(6):741-53). It appears that the ability of ORF252 to protect genome stability is more "primordial" as the information for self-assembly is all contained in the protein structure without the need for interactions with damaged DNA. This feature provides ORF252 with the advantage of being less restricted in its ability to repair DNA and guarantee genome stability. Self-assembly of ORF252 in toroidal structures raises the interesting possibility of non-chemical signaling between the protein and DNA, possibly through biological quantum entanglement between the electron clouds of toroids of DNA and the electron clouds on the surface of toroidal ORF252 (for reference on biological quantum entanglement between electron clouds of nucleic acids, see: arxiv.org/abs/1006.4053). In the context of this invention, toroidal structures of DNA and proteins such as ORF252 become entangled because of their spatial geometry; this phenomenon is not dissimilar from the quantum entanglement at the level of the protein tubulin in neuron microtubules that is thought to be at the basis of human consciousness (doi: 10.1142/S0219635214400093). It is also consistent with the recent paper entitled "Is the Fabric of Reality Guided by a Semi-Harmonic, Toroidal Background Field?" (Symbiosis, 2018, 8; 1-15). It is interesting to notice that DNA itself is endowed with an intrinsic degree of consciousness (ISSN: 1944-6934: 4(20):7-30 (2011)) that obviously does not rely upon quantum entanglement at the level of tubulin. It is also interesting to notice that ancient viruses may have been responsible for the onset of consciousness in humans (doi: 10.1016/j.cell.2017.12.024) and, therefore, it is plausible that the intrinsic consciousness of the DNA of viruses and humans may have become entangled at different levels. As far as the role of ORF252 in the context of DNA repair is concerned, it is worth noticing that ORF252 binds RecA and stimulates homologous recombination reactions. Not surprisingly, human RAD52, an evolutionary derivative of ORF252, was recently defined "a novel player in DNA repair in cancer and immunodeficiency" and was attributed a tumor suppressor function (doi: 10.3324/haematol.2016.155838). These functions of ORF252/RAD52 are consistent with a recent clinical observation in a case of multiple myeloma (doi: 10.3844/ajisp.2019.5.9). It is also worth noticing that RAD52 was demonstrated to suppress HIV-1 infection in a manner independent of its ability to repair DNA double strand breaks through homologous recombination (doi: 10.1080/10408398.2017.1339665). Although there are no direct evidences for a role of ORF252 protein in suppressing retroviral infections, since this activity resides in the DNA-binding and self-interaction domains of RAD52 that are homologous to ORF252, it is tempting to speculate that ORF252 of phage u136 may also have anti-retroviral activities by binding to retroviral cDNA and suppressing integration of the infecting virus.

The inventor discovered that the proteins encoded by the uvr genes of *Arthrospira* and *Lactococcus lactis* (Ruggiero M. (2020) bioRxiv. doi.org/10.1101/2020.07.21.214676) share significant similarities and homologies with ORF252 as well as with another protein of paramount importance in human DNA repair, the UV excision repair protein RAD23 homolog B, that is encoded by the gene RAD23B. This is a multiubiquitin chain receptor involved in modulation of proteasomal degradation. RAD23B binds to polyubiquitin chains and is capable to bind simultaneously to the 26S proteasome and to polyubiquitinated substrates and to deliver ubiquitinated proteins to the proteasome. It plays a role in endoplasmic reticulum-associated degradation (ERAD) of misfolded glycoproteins by association with Peptide-N-glycosidase and delivering deglycosylated proteins to the proteasome and it is involved in global genome nucleotide excision repair (GG-NER) by acting as component of the Xeroderma pigmentosum, complementation group C (XPC) complex. Cooperatively with Centrin-2 CETN2 stabilizes XPC and may protect XPC from proteasomal degradation. The XPC complex is the first factor bound at the sites of DNA damage and together with other core recognition factors, XPA, Replication Protein A (RPA) and the Transcription factor II Human (TFIIH) complex, is part of the pre-incision (or initial recognition) complex. The XPC complex recognizes a wide spectrum of damaged DNA characterized by distortions of the DNA helix such as single-stranded loops, mismatched bubbles or single-stranded overhangs that are lesions typically caused by exposure to electromagnetic radiations. The orientation of XPC complex binding is crucial for inducing a productive NER. XPC complex recognizes and interacts with unpaired bases on the undamaged DNA strand which is followed by recruitment of the TFIIH complex and subsequent scanning for lesions in the opposite strand in a 5'-to-3' direction by the NER machinery. In the context of the present invention, the region of interest is between residues 237 and 409.

The regions where the homologies between the four proteins (UvrABC system protein B of *Arthrospira platensis*, UvrABC system protein B of *Lactococcus lactis* subsp. *lactis*, human RAD23, and viral ORF252) are particularly evident are described in (Ruggiero M. (2020) bioRxiv. doi.org/10.1101/2020.07.21.214676) where they are highlighted by the similarity of the amino acids, the hydrophobicity profiles, and the presence of polar residues. It is important to notice that the peculiarity of this invention resides in the very precise ratio of Lactococci and phage u136 as evidenced in Tables 3 and 4. In the context of this invention, the high degree of similarity, hydrophobicity, and presence of polar residues that the inventor discovered in these particular regions of the four proteins is responsible for the transfer of information between bacteria, phages and human cells. This is particularly evident when comparing the human and the viral protein where the sequence of hydrophobic and polar residues shows a very significant degree of homology (for details, see Ruggiero M. (2020) bioRxiv. doi.org/10.1101/2020.07.21.214676).

EXAMPLES

In accordance with the invention, a product in an illustrative embodiment is comprised of the following ingredients and the following method for its manufacture.

The following method is for 1 L (liter). The procedure can be scaled up indefinitely.

Warm carbonated mineral water (1 L) with the chemical and radioisotope formula described in 7.1.1. up to 39° C. (Celsius)

Add 40 g (grams) of *Equisetum arvense*

Add 40 g of white sugar for human consumption

Add 15 mL of lemon juice for human consumption

Add 10 mL of apple cider vinegar for human consumption

Add 45 g of *Arthrospira* described in 7.1.2.1

Add 10 mg of proprietary probiotic blend described in 7.1.2.2

Gently mix the solution by stirring at 0, 12, 24, and 36 h

Maintain the temperature between 36° C. and 39° C. for 48 h

After 48 h incubation, gently mix the solution and proceed with freeze-drying

Collect the material from the lyophilizer and inspect the product; it should have an uniform, fine, greenish pulviscular aspect Place it in a suitable container and weigh it (tare and gross)

Label the container with product name, item #, lot #, date, net weight and expiration date Proceed with encapsulation.

Clean and clear the working area of all components not to be used for current run Clean and set up the capsuling machine before its use for the current run Bring all components on/near the capsuling bench Fill in the worksheet where needed with component's batch number, number of capsules used, amount of product used Verify technical data sheet of the empty capsules Verify by visual inspection the capsules, the bottles and the lids for their integrity Capsule the product and verify capsule weights for accuracy; adjust the capsuling machine if needed Complete the packaging record Clean the working area and record the necessary information It will be understood that various modifications may be made to the embodiments and examples disclosed herein. Therefore, the description and examples should not be construed as limiting, but merely as exemplification of the various embodiments. Those skilled in the art will envision other modifications within the scope and spirit of the claims appended hereto.

The following examples are provided to illustrate certain immediate aspects of the disclosure but should not be construed as limiting the scope of the disclosure.

Herein, it is demonstrated the efficacy of a product (supplement) manufactured according to the processes and methods that are the object of this invention in protecting against the harmful effects common electromagnetic fields, thus improving the quality of sleep, dreaming and fighting anxiety in subjects exposed to common electromagnetic fields. The efficacy is demonstrated by subjective observations (testimonials) and objective measures that were consistent with, and provided a physiologic support to the subjective observations.

Testimonials

The product, commercialized after the filing of the provisional patent application related to this invention, was used by a number of subjects of different gender, age and background. The excerpt of the testimonials listed below are representative of a number of observations describing identical, or very similar, effects associated with consumption of the product. These testimonials have been slightly edited only for the purpose of preserving privacy. No alteration to the substance of the testimonials has been made.

I have been taking the product, recommended by a friend, for a week now. I noticed my sleep has really improved. Normally when we go to our Beach House up North, I have this amazing deep sleep. I have noticed the same amazing quality sleep, since taking the product. So happy I found this.

I just started on the product and feel much better, It is the same feeling I get when being in the Mountains to our Cabin during holidays. Feeling calm and relaxed, clear headed and energized. We really don't know how the city living affects us. It's a worry, so happy I found this product.

I am an insomniac, like to watch movies on my ipad and then can't sleep. I can't be bothered with the blue blocker glasses really. Since taking the product, I don't have a problem going to sleep and sleeping through the night deeply. I wake up refreshed and ready to go. Thanks.

I recently had a CT spect scan for my back injury, and was worried about all the radiation. I feel I have found something that will counter this and repair any radiation damage. I am taking the product to protect me against those effects.

My city has heavy radiations. I worry a lot. This products makes me feel better. Thank you doctor.

I have researched EMF sensitivity for years, and I understand EMF poisoning well. This product assisted me greatly with my own sensitivity. I have long suffered from severe migraines, which virtually disappeared when I took the product. The migraines came back as soon as I ran out of capsules, which prompted me to quickly obtain some more.

Once I started taking the capsules I noticed much better sleep. I was more refreshed and less irritable because my sleep had improved. As a younger woman, I also noticed my skin appearance improve, with fewer spots and blemishes.

Improvements noticed were: More rejuvenating sleep; possibly more dreaming, and/or more vivid dreams; increase in health of GI Tract, with bowel evacuations being 2-3 times per day, with well-formed but soft stools; feeling a bit less stressed each day, with it being easier to maintain a slower respiration rate when doing focused, relaxing breathing; less brain fog and small increase in mental clarity.

I usually have poor sleeping habits, but I had deeper sleeps with better recovery while using the product. I used to get no REM sleep, but once I started on the capsules I had regular REM sleep within a few days.

I never used to worry about electromagnetic radiation, but once I tried the product, I could see the improvements. I felt better, slept better, and was more positive in my outlook. My cell phone never leaves my side, so it feels good to know I am benefitting from the radiation resistant properties of the product.

Objective Measures

Figure 1:
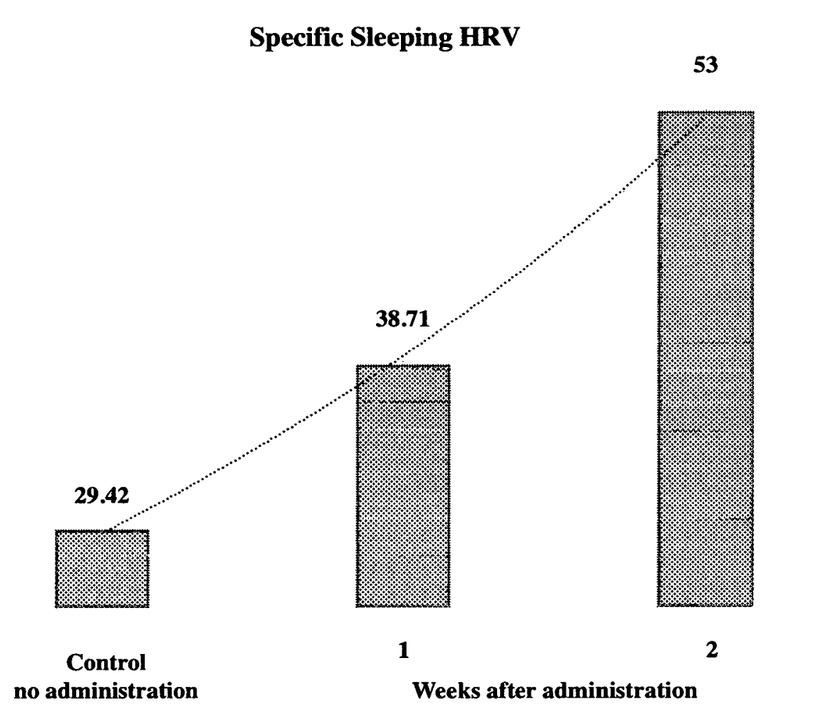

Objective measures reported by subjects using the product described above support the hypothesis that the molecular mechanism of action described in this document is at work under real-life conditions. These subjects, who, just like the subjects of the testimonials quoted above, were exposed to common environmental electromagnetic fields (house appliances, wiring, wireless communication devices), observed significant increase of heart rate variability (HRV) associated with regular consumption of the product. Such an increase was particularly evident during sleep. Considering that electromagnetic fields such as those of wireless communication affect HRV (Ruggiero, M. (2021) American Journal of Immunology, 17(1), 14-24), and considering that high HRV is associated with reduced morbidity and mortality and improved psychological well-being and quality of life (Ruggiero, M. (2021) American Journal of Immunology, 17(1), 14-24), these observation seem to indicate a protective effect against the harmful effects of electromagnetic fields. FIG. 1, shows the increase in sleep specific HRV in a subject assuming the product for three weeks. The subject was a female, age 29, height 162 cm, weight 65 kg who lives in a suburban city environment with medium density housing, has 2 mobile phones in the bedroom, and a wifi router close by. HRV was measured by an Apple watch with Bluetooth functionality enabled. This example is representative of several other that gave qualitatively superimposable results.

The invention claimed is:

1. A process to manufacture a lyophilized probiotic powder composition aimed at protection from harmful effects of electromagnetic radiations, comprising the steps of:

providing a medium for the growth of probiotic microbes constituted by carbonated radioactive mineral water whose radioactivity is due to $^{226}$Radium at 152 mBq L$^{-1}$ and $^{238}$Uranium at 217.7 mBq L$^{-1}$, comprising: 40 g/L *Equisetum arvense*, 40 g/L white sugar, 15 ml/L lemon juice, and 10 ml/L apple cider vinegar;

inoculating the medium with *Arthrospira platensis* at 45 g/L and 10 mg/L of a probiotic mixture comprising: *Lactobacillus paracasei, Lactobacillus casei, Lactobacillus helveticus, Lactobacillus kefiranofaciens, Lactobacillus plantarum, Lactobacillus gallinarum, Lactobacillus delbrueckii, Lactobacillus rhamnosus, Lactobacillus salivarium, Lactobacillus acidophilus, Lactobacillus farraginis, Lactobacillus antri, Lactococcus lactis, Lactococcus diacetylactis, Lactococcus cremoris, Bifidobacterium infantis, Bifidobacterium bifidum, Bifidobacterium lactis*, and *Bifidobacterium longum*;

cultivating *Arthrospira platensis* and the probiotic mixture in the medium comprising radioactive carbonated mineral water with *Equisetum arvense* at a temperature range of 36° C. to 39° C. for 48 h, with stirring at 0, 12, 24, and 36 h, to produce a probiotic composition;

harvesting the probiotic composition from the medium;

lyophilizing the probiotic composition to produce a lyophilized probiotic powder; and encapsulating the lyophilized probiotic powder.

* * * * *